United States Patent [19]

Allington et al.

[11] Patent Number: 5,080,785
[45] Date of Patent: Jan. 14, 1992

[54] CHROMATOGRAPHIC SYSTEM

[75] Inventors: Robert W. Allington; John N. Jones, both of Lincoln, Nebr.

[73] Assignee: Isco, Inc., Lincoln, Nebr.

[21] Appl. No.: 523,475

[22] Filed: May 15, 1990

Related U.S. Application Data

[62] Division of Ser. No. 358,447, May 30, 1989, abandoned, which is a division of Ser. No. 73,079, Jul. 13, 1987, Pat. No. 4,882,063.

[51] Int. Cl.$^5$ .............................................. B01D 15/08
[52] U.S. Cl. .................................. 210/198.2; 210/101; 210/137; 210/143; 366/152; 366/160; 366/162
[58] Field of Search ....................... 366/152, 160, 162; 210/656, 659, 101, 137, 143, 198.2

[56] References Cited

U.S. PATENT DOCUMENTS 3,934,456  1/1976  Munk ................................ 210/198.2
4,043,906  8/1977  Helmer .............................. 210/741
4,437,812  3/1984  Abu-Shumays et al. ......... 210/198.2
4,752,385  6/1988  Wilson ............................... 210/656

Primary Examiner—Ernest G. Therkorn
Attorney, Agent, or Firm—Vincent L. Carney

[57] ABSTRACT

To prevent the solvents forming a gradient from mixing at the wrong place and to provide for accurate composition at start of the gradient in spite of solvent pressure variations, a microliquid or supercritical fluid chromatograph includes a combined mixer and pressure detector in which equal pressures of the two solvents in the gradient are detected by displacement of a ferromagnetic poppet in the mixing chamber. The poppet serves as a stop for the final solvent until the pressures are substantially equal and then its movement is detected by a circuit related to a linear variable differential transformer. The signal energizes a circuit which drives one of the sensing coils to drive the poppet during the gradient to provide mixing.

20 Claims, 5 Drawing Sheets

CHROMATOGRAPHIC SYSTEM

This application is a division of application Ser. No. 07/358,447, filed May 30, 1989, now abandoned, which, in turn, is a division of Ser. No. 073,079, filed July 13, 1987, now U.S. Pat. No. 4,882,063.

BACKGROUND OF THE INVENTION

This invention relates to the formation of elution gradients for gradient elution chromatography.

It is known in gradient elution chromatography to pump two or more different fluids to a mixer and to use a magnetic stirrer to mix the two fluids. The start and composition of the gradient is controlled by a programmer.

In the prior art gradient systems of this class, the gradient program is initiated in response to a timer or by manual initiation or by a fixed program for repetitive runs. The mixer operates independently of the program control.

The prior art apparatus and methods for establishing the gradient have several disadvantages, such as: (1) the pumps for the fluids may be at different pressures at the time of the start of the chromatographic run and, in such a case, the gradient is distorted at the start because the uneven pressure causes the fluid from the lower pressure source to be held back or even for the fluid from the higher pressure source to flow into the lower pressure source; and (2) under some circumstances, it is difficult to obtain suitable mixing unless a reservoir is used that is too large for certain shaped gradients. These disadvantages are more significant in microliquid chromatography and supercritical chromatography. The pumps used for these two types of chromatography are usually single-stroke syringe pumps whose relatively large fluid volume aggregates the first disadvantage, above.

SUMMARY OF THE INVENTION

Accordingly, it is an object of the invention to provide a novel chromatographic system.

It is a further object of the invention to provide a novel technique for gradient elution chromatography.

It is a still further object of the invention to provide a novel technique for starting the flow of a gradient in gradient forming.

It is a still further object of the invention to provide a novel differential pressure sensor.

It is a still further object of the invention to provide a novel combined check valve and mixing system.

It is a still further object of the invention to provide a novel gradient forming technique in which the gradient is not started until the pressures of each of the fluids forming the gradient are equal at a point where the fluids are mixed.

It is a still further object of the invention to provide a technique for economically and efficiently mixing fluids in a gradient elution chromatographic system.

It is a still further object of the invention to provide a gradient elution chromatographic system in which the gradient program is not started until the pressures of at least two fluids that are to be mixed to form the gradient are substantially equal.

It is a still further object of the invention to provide novel techniques for gradient elution chromatography that are particularly useful as part of microliquid chromatography or supercritical fluid chromatography systems.

In accordance with the above and further objects of the invention, apparatus is provided for processing fluids in a gradient elution chromatographic system. Generally, the fluid comes from multiple sources and is a combination of different solvents pumped by refillable single-stroke syringe-type pumps to a mixer and from the mixer to a chromatographic system that includes a sample injector, a column and at least one detector.

The apparatus includes a differential pressure sensor which permits only the initial solvent to flow until the pressures behind each of the fluids are substantially equal. When the pressures of the fluids are equal, a signal is transmitted to the controller which: (1) starts a gradient run while permitting the proper composition of the gradient to flow; and (2) initiates stirring action within the apparatus for efficient mixing.

Advantageously, the apparatus includes a mixing chamber, a high permeability ferromagnetic member, sensing means for sensing the position of the high permeability member, and drive means for driving the high permeability member. The chamber has at least two inlets and an outlet to permit at least two fluids to enter the chamber and a combination of fluids to leave the chamber through the outlet. The high permeability member is movably mounted within the chamber to serve as a check valve element, pressure equality sensing element, fluid control element and mixing element.

To accomplish these purposes, the high permeability member is capable of assuming a plurality of positions within the chamber and of cooperating with the drive means and the sensing means. In one of the plurality of positions, the high permeability member blocks at least one of the inlets while permitting flow of at least one fluid through another inlet, the mixing chamber and the outlet. With this arrangement, a high initial fluid pressure causes the high pressure fluid to flow through the mixer but blocks flow from another source of lower pressure until the pressures of the fluids are approximately equal, at which time, the pressure balance permits both inlets to be open.

When one or more of the inlets are in the process of opening, the sensing means signals the start of the gradient program. This signal may also initiate the generation of pulses from a pulse generator to energize the drive means and thus move the high permeability element in a manner that causes mixing of the fluids flowing through the mixing chamber. The pulses may be applied to a coil around the outside of the mixing chamber to magnetically move the high permeability member.

The sensing means senses the equality of pressure in a plurality of fluids by sensing the position of the high permeability member. In the preferred embodiment, the position of the high permeability member is sensed by sensing the magnetic field created by a coil. The sensed field is altered by the characteristics of the flux paths as altered by the location of the high permeability member.

First, second and third coils cooperate with the high permeability member to sense characteristics of the flux path and one of the first and second coils is also used to drive the high permeability member during mixing. The first and second coils are oppositely wound coils on either side of the third coil. The third coil is energized with alternating current and induces oppositely phased potentials in the first and second coils during sensing of the pressure relationship of the fluids flowing through the mixing chamber. The first and second coils are electrically connected together so that the potentials induced in them are summed.

When the high permeability member is in a first position, it balances the potentials induced in the first and second coils and causes an unbalance when in a second position. This distinction is for the most part arbitrary, and useful mostly for purposes of explanation. It is actually only necessary that there be a change in the relative balance or unbalance between the first and second positions. When the high permeability member is in the second position, it shifts the flux paths between the first, second and third coils and thus creates an unbalance in the potentials induced in the first and second coils by the third coil. The high permeability member is in the second position when blocking the flow of at least one fluid and in the first position when the fluids are substantially equal in pressure and both flowing through inlets.

Because in the first position the potentials induced in the first and second coils are equal or nearly equal in amplitude, the difference is a low-amplitude signal indicating the start of a gradient. In the preferred embodiment, this signal is demodulated by a synchronous detector and differentiated to result in the signal starting the gradient.

From the above description, it can be understood that the apparatus of this invention has several advantages, such as: (1) it is economical in that it combines functions for mixing and starting the gradient; (2) it is capable of precisely starting a gradient in microliquid chromatography or supercritical liquid chromatography even though the initial solvent pump may be operating at a higher pressure than the final solvent pump; and (3) it provides mixing efficiently, economically, and without requiring much space.

SUMMARY OF THE DRAWINGS

The above noted and other features of the invention will be better understood from the following detailed description when considered with reference to the accompanying drawings, in which.

DETAILED DESCRIPTION

Figure 1:
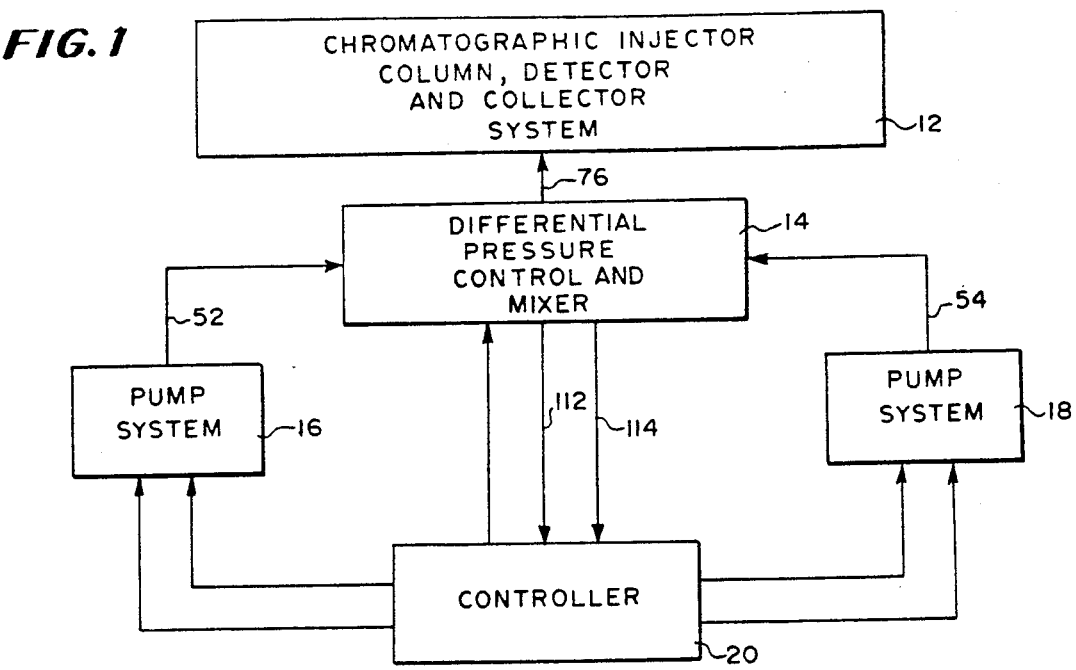
FIG. 1 is a block diagram of a chromatographic system in accordance with the invention.

In FIG. 1, there is shown a block diagram of a chromatographic system 10 having a chromatographic injector, column, detector and collection system 12, a differential pressure control and mixer 14, a first single-stroke syringe pump system 16, a second single-stroke syringe pump system 18 and a controller 20. Single-stroke syringe pumps usually are not refilled during a chromatographic separation; they are refilled between separations. The chromatographic system 10 is a gradient system in which the differential pressure control and mixer 14, the first and second single-stroke syringe pump systems 16 and 18 and the controller 20 are connected together to supply a programmed gradient to the chromatographic injector column, detector and collector system 12.

To provide gradient programming, the controller 20 is electrically connected to the first and second single-stroke syringe pump systems 16 and 18. The first and second single-stroke syringe pump systems 16 and 18 communicate with the differential pressure control and mixer 14 so that the controller 20 initiates the flow of first and second fluids to the differential pressure control and mixer 14 from the first and second single-stroke syringe pump systems 16 and 18 respectively prior to the initation of a gradient, with the fluid from one of the first and second single-stroke syringe pump systems 16 and 18: (1) flowing first through the chromatographic column; and (2) having a higher pressure than fluid from the other pump system at start up of pumping.

To start the flow of more than one fluid through the differential pressure control and mixer and thus initiate a gradient, the differential pressure control and mixer 14 determines when the pressures from the first and second single-stroke syringe pump systems 16 and 18 are substantially equal. When the pressures in the first and second fluids are substantially equal, the differential pressure control and mixer 14: (1) signals the controller 20 to initiate the gradient; and (2) signals the controller 20 to energize a mixer within the differential pressure control and mixer 14. In the preferred embodiment, controller 20 initiates that gradient formation and mixing action upon receiving a signal from the differential pressure control and mixer 14 indicating that the pressure from the first and second single-stroke syringe pump systems 16 and 18 are equal.

With this arrangement, the differential pressure control and mixer 14 communicates with a chromatographic injector, column, detector and collector system 12 to permit the flow of a carefully controlled gradient. It is particularly significant that the pressure is balanced before the gradient starts to the chromatographic injector, column, detector and collector system 12 because of the difficulty of starting the flow at the desired initial composition for the gradient in microliquid chromatography and supercritical fluid chromatography.

Figure 2:
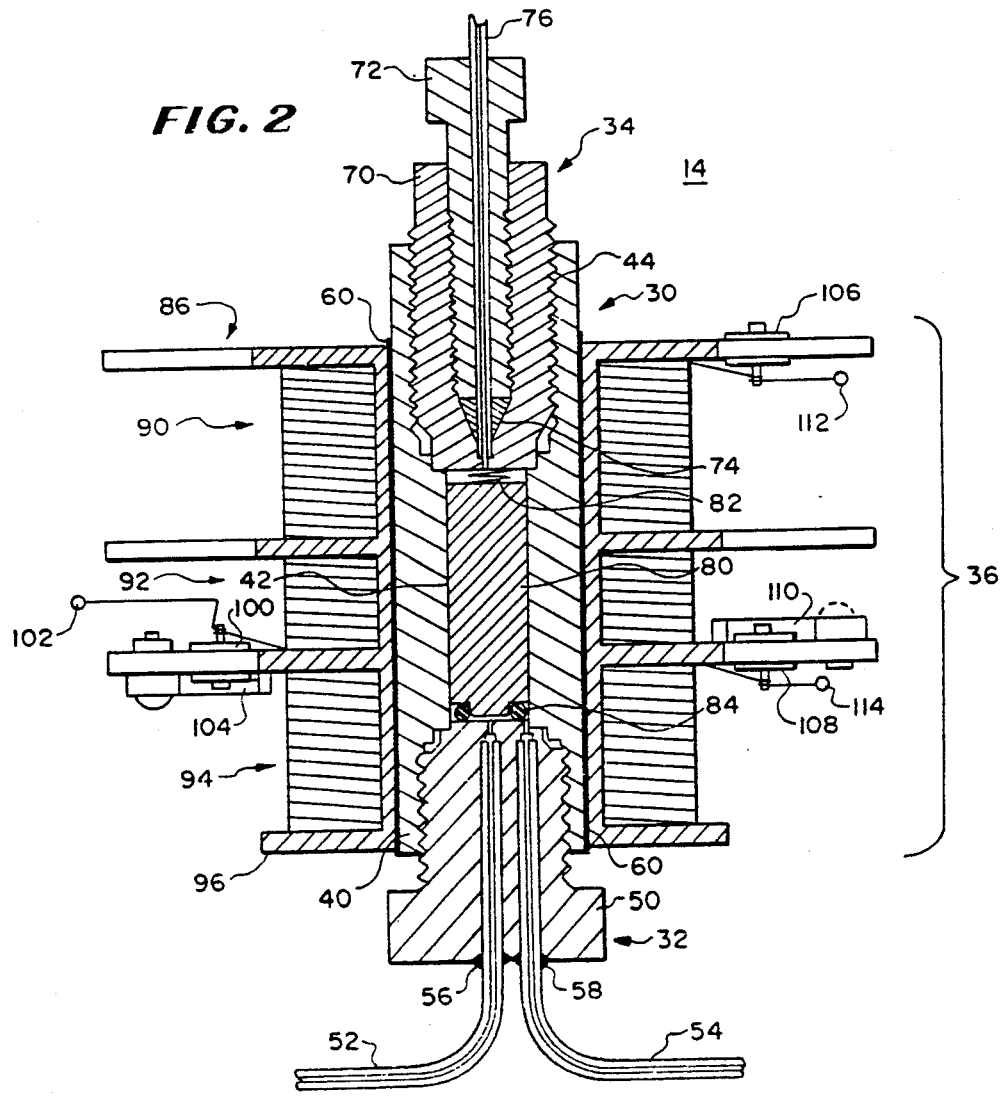
FIG. 2 is a sectional longitudinal view of apparatus in the chromatographic system of FIG. 1 for performing pressure measurement, gradient starting and mixing.

In FIG. 2, there is shown a sectional view of the differential pressure control and mixer 14, having a main body portion 30, an inlet fitting 32, an outlet fitting 34, and a sensing and control section 36. The main body portion 30 is a tubular stainless steel body having through it a continuous passageway with: (1) a first portion at 40 adapted to receive the inlet fitting 32; (2) a central chamber at 42 adapted to accommodate a sensing means, a mixer and a check valve; and (3) an outlet portion 44 including a tapped bore to receive the outlet fitting 34.

The main body portion 30 should be generally of non-magnetic material. In the preferred embodiment, it is made of non-magnetic, high electrical resistance stainless steel. The specific stainless steel in the preferred embodiment is sold under the trademark Nitronic 50 by Armco Steel Corporation, Advanced Materials Division, Baltimore, Md. However, any non-magnetic, high electrical resistance, low corrosion material may be used. In the case of stainless steel the specific shape is machined into a cylinder of stainless steel but other materials, if used instead of stainless steel, are shaped as appropriate for those other materials.

To receive fluid from the first and second single-stroke syringe pump systems 16 and 18 (FIG. 1), the inlet fitting 32 includes a reasonably high resistance, non-magnetic stainless steel plug 50 having an externally threaded shank and a larger cylindrical head. In the preferred embodiment, this is type 303 stainless steel. In addition to functional reasons, type 303 stainless steel's ease of machining was a reason for its selection. The externally threaded shank is adapted to be threaded into a tapped hole in the first portion 40 of the main body portion 30. When threaded in place, the stainless steel plug 50 has its longitudinal axis aligned with the longitudinal axis of the main body portion 30.

To permit fluids to enter the main body portion 30, the non-magnetic stainless steel plug 50 includes first and second openings, each having a diameter of approximately 1/16 inch and each extending through it from its head portion to its end where it communicates with the central chamber 42 of the body portion 30. These openings receive the first fluid from the first single-stroke syringe pump system 16 and the second fluid from the second single-stroke syringe pump system 18 respectively.

To receive the first fluid, the first opening extends along the longitudinal axis of the main body portion 30 and receives a non-magnetic tube 52 having an outer diameter of 1/16 inch and an inner diameter of 0.010 inches which tube extends to within a distance of approximately 1/16 inch of the end of the plug 50 where the plug 50 includes a 0.010 inch channel that connects the 1/16 inch opening to the central chamber 42. The tube 52 receives fluid from the first single-stroke syringe pump system 16 (FIG. 1) and applies it to the central chamber 42. When its pressure is substantially equal to the pressure of the second fluid the first and second fluids are mixed to form a starting gradient within the central chamber 42.

The second opening has dimensions substantially the same as the first opening in the plug 50 and receives a tube 54 similar to the tube 52 to provide communication between a source of the second fluid and the central chamber 42 through the tube 54. However, the second opening enters the central chamber 42 nearer the side wall of the chamber and is offset from the central axis of the stainless steel plug 50. The second opening is located near the side wall of the chamber 42 so that it is not blocked when the fluids are first pumped prior to the start of a gradient although the first opening may be blocked for a time in a manner to be described hereinafter.

The tubes 52 and 54 are sealed to the stainless steel plug 50 by gold solder at 56 and 58, respectively, in annular rings around each tube to provide a seal about the first and second openings in the stainless steel plug 50. With this arrangement, the tubing 52 and 54 carry fluid through the stainless steel plug 50 into the central chamber 42. This fluid may be at different pressures near the start of a chromatographic run but the differential pressure control and mixer 14 prevents mixing of the fluids to start the gradient until the pressures are equal and thus prevents distortion in the gradient caused by inequality of the pressures.

The outlet fitting 34 includes a stainless steel plug 70, a stainless steel long nut 72 and a stainless steel ferrule 74. The stainless steel plug 70: (1) is cylindrical; (2) has a threaded outer surface to engage threads in the outlet portion 44 of the main body portion 30; (3) extends downwardly to close the central chamber 42; (4) has within it a tapped hole extending along its longitudinal axis from its top to a location near its bottom into which tapped hole the stainless steel long nut 72 is threaded; (5) has a small channel along its longitudinal axis connecting the tapped hole and the chamber 42 at its bottom end; and (6) has a tapered portion between the tapped hole and the channel, which tapered portion is shaped to accommodate a stainless steel ferrule 74 that seals the stainless steel long nut 72 against the tapped hole of the plug 70.

The stainless steel long nut 72 has external threads to engage the internal threads of the tapped hole in the stainless steel outlet plug 70 and a central opening to receive the 1/16 inch outer diameter non-magnetic tube 76 which extends along its cental axis and through the stainless steel ferrule 74 to abut the outlet of the central conduit of the stainless steel plug 70 to thereby permit communication between the central chamber 42 and the chromatographic injector, column, detector and collector system 12 (FIG. 1). The outlet tube 76 is similar to the tubes 52 and 54 but carries fluid to the chromatographic injector, column, detector and collector system 12 (FIG. 1) from the central chamber 42 instead of carrying fluid to the central chamber.

The sensing and control section 36 includes a spring 82, an O-ring 84, a coil section 86 and a ferromagnetic high permeability plug which serves as a poppet 80. The poppet 80 is biased in one direction by the O-ring 84 and in the other by the spring 82 so that the O-ring normally seals the first inlet to the first fluid flowing through tube 52 from the central chamber 42 as described hereinafter.

To prevent flow of the first fluid until there is pressure equalization between the first and second fluids, the spring 82 and the O-ring 84 are related in their size and force needed to compress them so that the pressure of the second fluid, the weight of the poppet 80 and the spring 82 compress the O-ring 84 around the first inlet until the pressure of the first fluid is slightly greater than that of the second fluid at which time the force exerted by the first fluid is sufficient to overcome gravity and the spring bias and permit the first fluid to flow. Just before the first fluid starts to flow, the poppet 80 moves upward, decompressing O-ring 84. The decompression of O-ring 84 provides for a significant and detectible movement of poppet 80 at this time. When the first fluid starts to flow, its pressure does not drop below its immediately preceeding value because the spring and gravity forces on the poppet 80 remain the same as before and provide a constant throttling action. Thus, for practical purposes, the pressures may be considered to be equal because: (1) their differences vary only slightly; and (2) the difference does not change from the time just before the flow of the first fluid starts and the time during formation of the gradient.

The coil section 86 surrounds the poppet 80, being positioned to sense the position of the poppet 80 during pressure equalization and to drive the poppet 80 during mixing. For this purpose, the coil section is sufficiently close to the poppet 80 for magnetic coupling and not separated by any shunt path or shield for flux so as to be able to sense the poppet and drive it without excessive heating.

In the preferred embodiment, the poppet 80 is formed of ferromagnetic stainless steel which is sufficiently chemically inert to handle solvents used in liquid chromatography without damage and has a sufficiently high magnetic permeability to be capable of being driven and sensed with magnetic fields. Its coercivity should be sufficiently low to not retain significant magnetization. Its electrical resistivity is sufficiently high to prevent excessive eddy current loss. It is generally cylindrical to conform to the central chamber 42 but is smaller in dimensions so that there may be flow around it and it may move within the central chamber 42 for mixing action.

At the inlet end of the poppet 80, there is a reduced diameter boss extending from the main body of the poppet. It has a diameter greater than the inner diameter of the O-ring 84 and fits within it with the annular shoulder formed by the boss overlying the O-ring 84 and with the boss fitting within the O-ring 84. Generally, the diameter of the poppet 80 is within the range of 10 mils and one inch and has a diameter slightly less than the inner diameter of the central chamber 42. The ratio of length to diameter of the poppet 80 is greater than 0.25 to 1 and less than 20 to 1 but the length must be smaller than the length of the central chamber 42.

With these dimensions, the volume of space (free volume) able to accommodate fluid between the poppet 80 and the walls of the central chamber 42 is in the range of one to 2,000 microliters and in the preferred embodiment is 61 microliters. It is selected in accordance with good chromatographic practice to enable desirable gradient curves to be obtained. In the preferred embodiment, this 61 microliters is in the space between the 0.275 inch diameter central cavity in the main body portion 30 and the 0.268 inch diameter by 0.783 inch long poppet 80.

The conduits through the inlet fitting 32 which accommodate the tubes 52 and 54 are offset from each other so that the extending boss of the poppet 80 and the O-ring 84 block fluids, other than the initial fluid of the gradient while permitting the initial fluid to flow from the second pump and its reservoir. Consequently, they are spaced apart from each other by a length at least equal to the thickness of the O-ring 84 which is adjacent to the conduits through the inlet fitting 32. With this arrangement, upon the start of pumping, the fluid flows from the initial solution pump and reservoir through the differential pressure control and mixer 14 but the poppet 80 is held against the conduit in the inlet fitting 32 to prevent flow until the pressure is equalized in the tubing 52 and 54.

The spring 82 is a conical, non-magnetic, corrosion-resistant, wire spring having a diameter of 0.004 inch and, in the preferred embodiment, is made of Moleculoy. Moleculoy is available from Molecu-Wire Corporation at P.O. Box 495, Farmingdale, N.J. 07727. It must resist compression with an initial force at least sufficient to prevent the poppet 80 from adhering to the wall of central chamber 42.

The spring 82 is designed to have a load at minimum compression sufficient to urge the poppet 80 against the O-ring 84 so that there is no unnecessary looseness of the poppet 80, but not so large at either maximum or minimum compression as to prevent the movement of the poppet during mixing of the gradient or to prevent release of the fluid which is combined with the initial fluid to start the gradient. It is desirable for it to not be effected by magnetic fields.

The O-ring 84 has a diameter across the entire O-ring 84 substantially the same size as the diameter of the extended boss portion of the poppet 80 and a cross sectional diameter of the O-ring 84 slightly larger than the length of the extended boss portion of the poppet 80 so that when the poppet 80 is moved against the inlet fitting 32, the O-ring 84 is compressed to form a liquid-tight seal around the poppet boss and on the inlet fitting to prevent fluid from the final gradient pump and reservoir from being pumped through the tube 52 to the outlet of the differential pressure control and mixer 14. The diameter of the O-ring 84 is sufficiently small so that it does not block the outlet of the tube 54, thus permitting it to flow around the poppet 80 to exert back pressure on the poppet 80 against the O-ring 84.

The O-ring 84 should have a resilience within a range that enables the back pressure of the fluid within the outlet tubing 76 to cause the poppet 80 to compress the O-ring 84 and thus seal the inlet to the central chamber 42 from the tube 52 when the back pressure from the initial fluid is at least larger than the pressure in the other fluid or fluids by 50 percent of the operating pressure. On the other hand it should not be so large as to prevent the poppet 80 from being moved when the pressure difference between the fluids is within 50 percent of the number of pounds per square inch as the operating pressure of the chromatographic system during a gradient elution run. In the preferred embodiment, O-ring 84 is made of Kalrez. Kalrez is available from E. I. DuPont de Nemours Co, Wilmington, Del.

To sense the position of the poppet 80 during the equalization of pressure and to drive the poppet 80 for mixing during the gradient, the coil section 86 includes a first coil 90, a second coil 92, a third coil 94 and a spool 96. The spool 96 separates and insulates the first, second and third coils 90, 92 and 94 from each other and holds them in juxtaposition with respect to the main body portion 30. These three coils form three cylinders coaxial with the central axis of the main body position 30 and the poppet 80 and circumscribes them.

The second coil 92: (1) is 30-gauge insulated copper wire wound to a 1.3 inch outer diameter about the spool 96; (2) is electrically connected to ground at one end (not shown in FIG. 2) and to a post 100 at the other end; (3) is centrally located with respect to the poppet 80; and (4) has the first and third coils 90 and 94 on either side of it spaced longitudinally along the longitudinal axis of the differential pressure control and mixer 14. The post 100 is fastened to the spool by a threaded nut and covered on one side by a cover 104. A conductor 102 is electrically connected to receive alternating current potential for application to the second coil 92 in a manner to be described hereinafter.

The first and third coils 90 and 94 each have one end grounded and the other end electrically connected to the connector posts 106 and 108, respectively. They are connected in opposite directions so that the electromagnetic field set up by the second coil 92 induces potentials which have polaraties of opposite signs and thus form a differentially connected pair. The connector post 106 for the first coil 90 is electrically connected to a conductor 112 and the connector post 108 is electrically connected to a conductor 114, with the two terminals being electrically connected together so that the voltages across the first and third coils 90 and 94 due to the energizing of the second coil 92 oppose each other and thus one voltage is subtracted from the other. A cover 110 covers the connector post 108.

The wire in the first coil 90 is 0.0126 inch diameter (28-gauge) insulated copper wire wound to a diameter of 1.300 inch. The wire in the third coil 94 is 0.010 (30-gauge) insulated copper wire wound to a diameter of 1.30 inch. The conductor posts 100, 106 and 108 are made of brass and bolted onto fins of the spool, with two of them being covered by aluminum covers 104 and 110 also bolted onto fins of the spool.

With this arrangement, when the poppet 80 is forced downwardly so that its extending boss abuts the outlet leading from the tubing 52 and the O-ring 84 seals fluid against the face of the inlet fitting 32, the field from the second coil 92 induces a small amount more potential in the third coil 94 than in the first coil 90, so when these potentials are subtrated, there is a remaining potential of signal from the dominance of the third coil 94 at the location where conductors 112 and 114 are connected. When the poppet 80 is moved by the force of the first fluid and the elastic force of compressed O-ring 84 in the event of pressures in the tubing 52 and 54 that are close together indicating a close to equilibrium condition, the motion of the poppet 80 changes the flux field to result in a change of the potential or signal.

Similarly, the poppet 80 is sufficiently long and extends sufficiently far into the first coil 90 so that when the first coil 90 receives energetic pulses during the gradient run, the pulses through the first coil 90 are able to drive or move the poppet 80 causing it to mix fluid as it flows through the central chamber 42 for an evenly mixed gradient.

The permeability of the poppet 80 must be greater than one and it should be sufficiently high to be moved by the field generated from the first coil 90. It should be spaced from the first, second and third coils 90, 92 and 94 in a perpendicular direction by no more than two inches and have a mass sufficiently low to be moved by the field of the first coil 90 and sufficiently high to mix the fluid in the chamber 42, whereby adequate mixing is obtained.

In the preferred embodiment, the stainless steel plug 70, long nut 72, ferrule 70 and poppet 80 are ferromagnetic to form a flux path for the flux from the first coil 90 that is capable of moving the poppet 80 to close the gap formed when it is moved away from the outlet by the spring 82. For this purpose, they are made of type 450 stainless steel as described in U.S. Pat. No. 3,574,601 and sold by Carpenter Technology Corporation, 101 West Bern Street, Reading, Pa. 19601, under the designation Carpenter custom 450. This steel has high electrical resistance and corrosion resistance.

Figure 3:
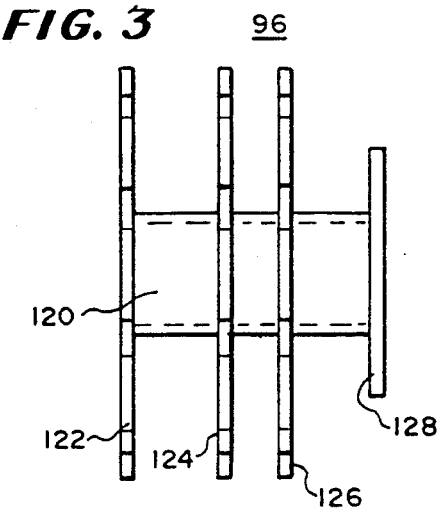
FIG. 3 is a side elevational view of a coil holding portion of the embodiment of FIG. 2.

In FIG. 3, there is shown a side elevational view of the spool 96 having a central tubular cylinder 120 and first, second, third and fourth radially extending retainer walls 122, 124, 126 and 128 respectively for the first, second and third coils 90, 92 and 94 (FIG. 2). The spool 96 is formed of aluminum with each of the first, second, third and fourth radially extending retainer walls 122, 124, 126 and 128 having smooth aluminum surfaces for holding the first, second and third coils 90, 92 and 94 (FIG. 2) within them.

At locations above the coils 90, 92, and 94, the retainer walls support the conductor posts 100, 106 and 108 (FIG. 2) and fins to increase air circulation. Spool 96 is made of aluminum because of aluminum's high thermal conductivity. For electrical insulation of main body portion 30 from spool 96, a mylar sheet 60 is wrapped around main body portion 30, between it and spool 96.

Figure 4:
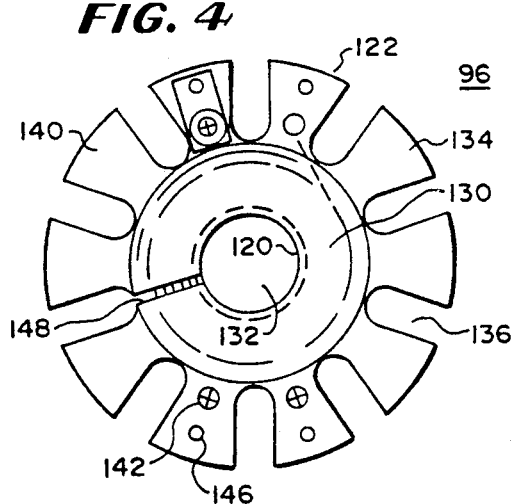
FIG. 4 is an end view of the coil holding spool of FIG. 3.

In FIG. 4, there is shown an end view of the spool 96 showing the first retaining wall 122 with a smooth portion 130, a tubular center 132 and a plurality of extending fins 134. The tubular center 132 is sized to conformingly receive the cylindrical main body portion 30 (FIG. 2) and the smooth portion 130 to support one side of the first coil 90 (FIG. 2). The extensions 134 contain slots such as the one shown at 136 to permit greater convection currents for cooling. As shown in FIG. 4, the individual radially extending portions such as 140 which are interleaved between the slots such as slot 136 are spaced approximately 0.796 inch apart center to center at the periphery and some of them include apertures such as 142 through which conductors may pass and bolt holes 146 positioned above them to which a conductor terminal may be mounted.

To prevent any currents induced by the alternating current field, a slot or air gap 148 extends through the spool 96 so that there is no complete conductive path around the spool 96 for current to flow. This air gap 148 extends through the entire spool 96. In the preferred embodiment, this air gap 148 is 0.020 inch.

Figure 5:
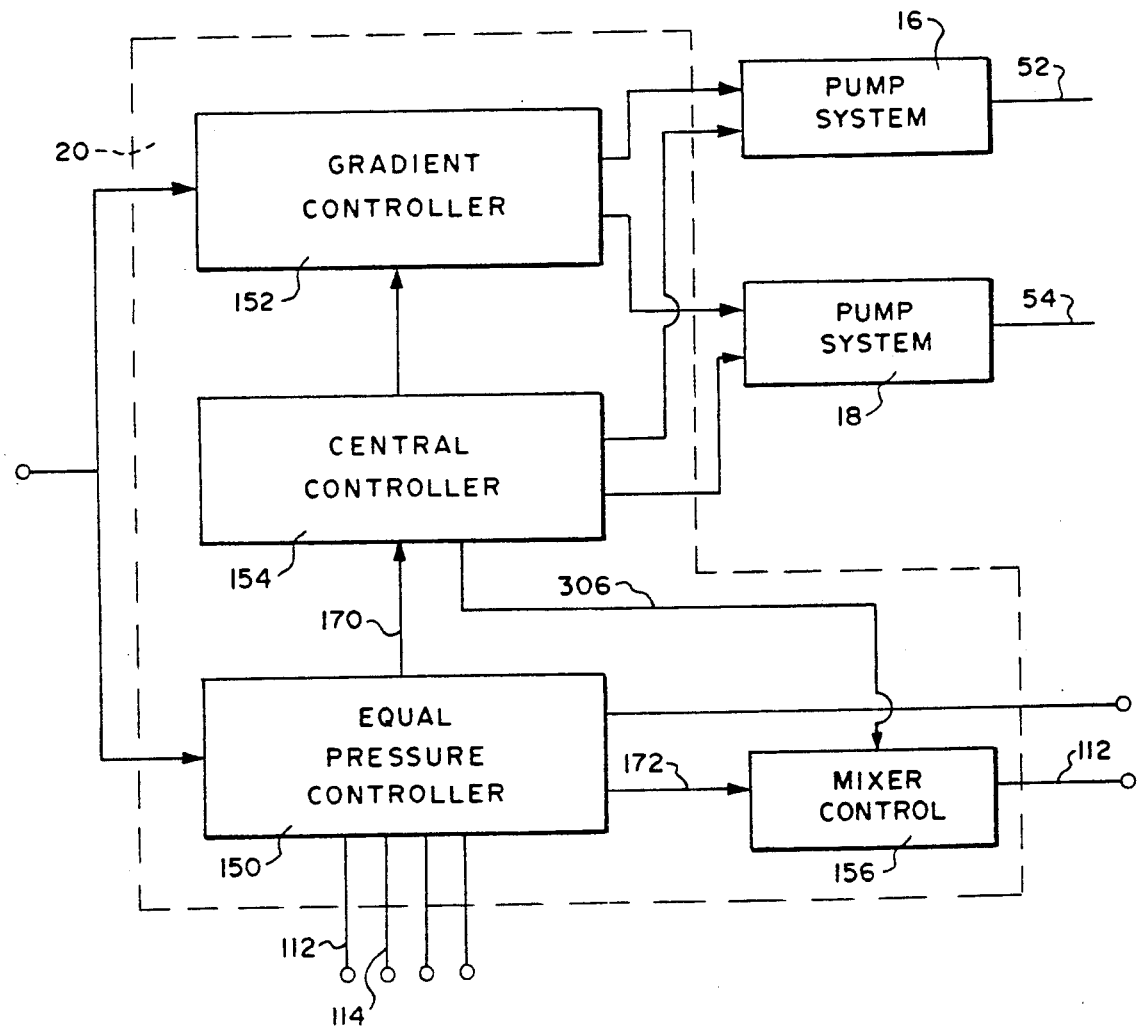
FIG. 5 is a block diagram of a gradient starting and mixing system used in the embodiment of FIG. 1.

In FIG. 5, there is shown a block diagram of the controller 20 connected to the first and second single-stroke syringe pump systems 16 and 18. As shown in this view, the controller 20 includes an equal pressure controller 150, a gradient controller 152, a central controller 154 and a mixer control 156. In the preferred embodiment, the first and second single-stroke syringe pump systems 16 and 18 are high-pressure syringe pumps which pump liquid in the range of 200 microliters per minute or less for use in microliquid chromatography and 500 microliters per minute or less for supercritical fluid chromatography.

The first and second single-stroke syringe pump systems 16 and 18 and the gradient controller 152 may be of the type described in U.S. Pat. No. 3,398,689 to Robert W. Allington. Pressurizing and running the system may be done in a number of different ways including those described in U.S. Pat. No. 4,422,942. If the system is used for supercritical fluid operation, two constant pressure pump controllers and motor drives of the type described in U.S. Pat. No. 3,985,467 to P. Lefferson may be used. In either event, the system may be used together with a gradient programmer and controller such as that described in the aforesaid U.S. Pat. No. 3,398,689.

Moreover, a syringe type pump such as that disclosed in U.S. Pat. No. 4,422,942 to Robert W. Allington, may be used instead of the reciprocating pump described in the aforesaid U.S. Pat. No. 3,985,467. The disclosure of these patents are incorporated therein.

The mixer control 156 receives a signal from the equal pressure controller 150 on conductor 172 or from the central controller 154 or conductor 306 and generates power pulses in response thereto for application to the differential pressure control and mixer 14 to energize the first coil 90 with unipolarity pulses which alternatively attract and release the poppet 80 (FIG. 2). The movement of the poppet 80 causes fluid to be mixed within the central chamber 42 (FIG. 2). The mixer control 156 has its action terminated by a signal on conductor 306 from the central controller 154 indicating the end of the chromatographic run.

Figure 6:
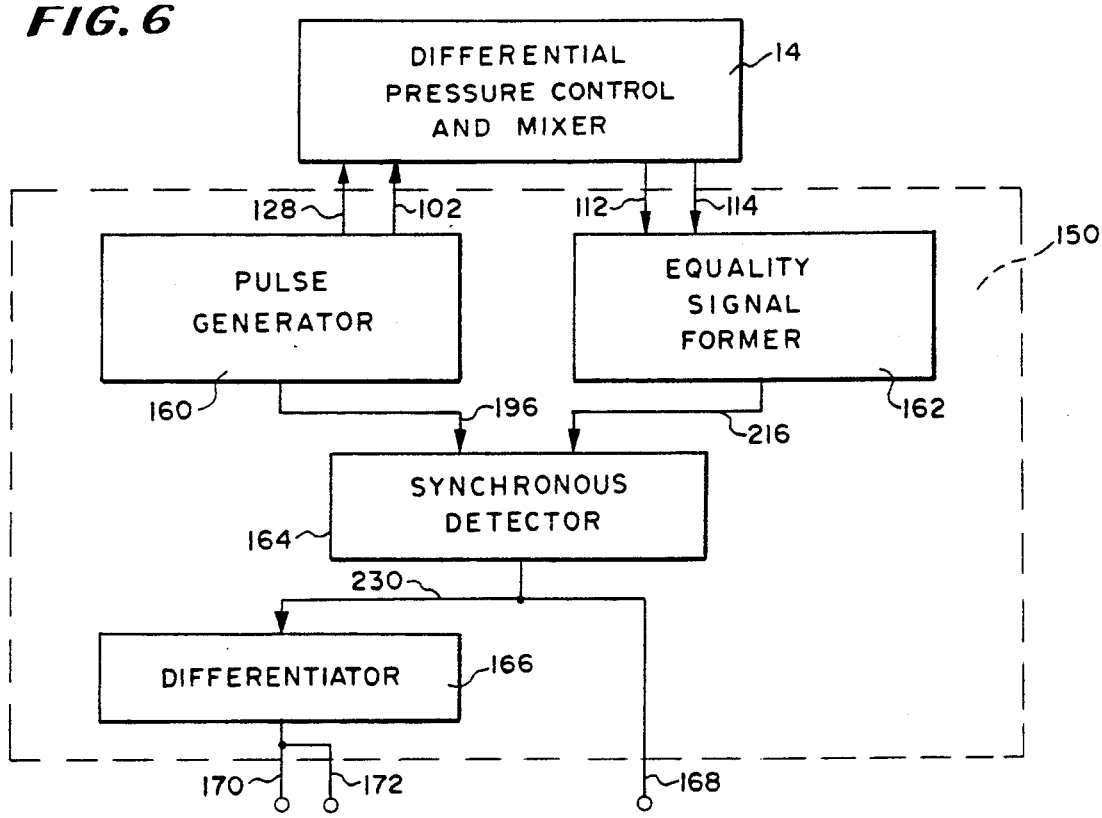
FIG. 6 is a block diagram of certain control circuitry used in the gradient starting system of FIG. 5.

In FIG. 6, there is shown a block diagram of the equal pressure controller 150 connected to the differential pressure control and mixer 14 and having an alternating current or AC generator 160, an equality signal former 162, a synchronous detector 164 and a differentiator 166.

To sense the position of the poppet 80 (FIG. 2) within the differential pressure control and mixer 14, AC generator 160 is electrically connected to the differential pressure control and mixer 14 to which it supplies a sensing AC supply and to the synchronous detector 164 to which it supplies synchronized pulses for detection purposes. The differential pressure control and mixer 14 is electrically connected to the equality signal former 162 to which it supplies an AC sensing signal of variable phase and amplitude in response to the position of the poppet 80 (FIG. 2) and an AC supply potential from the AC generator 160. The equality signal former 162 senses the position of the poppet 80 and supplies signals to the synchronous detector 164 related to that position.

To provide a DC-level signal indicating the position of the poppet 80 (FIG. 2) and to separate this signal from noise, the synchronous detector 164 is electrically connected to the AC generator 160 and to the equality signal former 162 to receive phase-reference pulses from AC generator 160, to receive a variable phase and amplitude signal from equality signal former 162, and to detect from these two signals the position of the poppet 80 (FIG. 2).

The output of the synchronous detector 164 is electrically connected to: (1) the differentiator 166, which generates a pulse indicating the equal pressure condition at which a gradient is to be supplied; and (2) an output conductor 168 indicating more generally the position of the poppet 80 (FIG. 2). Preferably, the differentiator 166 produces the second derivative of the output indicating the poppet position on conductors 230 and 168. Pressure equality is indicated by a decrease in the slope of the poppet position output versus time, and a second derivative of a slope change is a pulse. Thus, pressure equality is indicated by a pulse.

The differentiator 166 is electrically connected to: (1) the central controller 154 (FIG. 5) through a conductor 170 to start the central controller 154 through its programmed sequence which causes the first and second pumping systems 16 and 18 (FIG. 1) to supply the programmed gradient; and (2) the mixer control 156 (FIG. 5) through a conductor 172 to cause the mixer control 156 to generate power pulses for application to the first coil 90 (FIG. 2) for energizing the poppet 80 (FIG. 2) to begin its mixing action.

Figure 7:
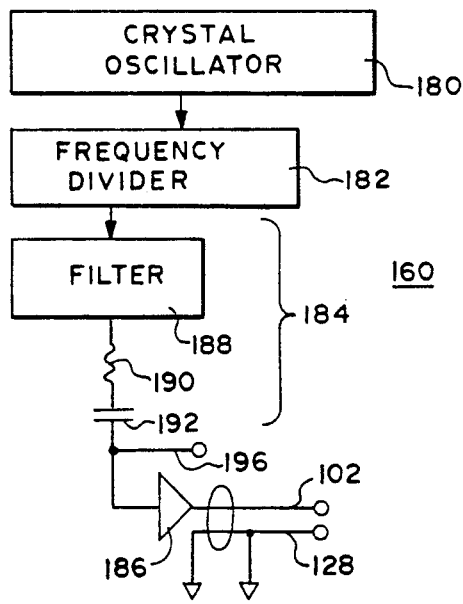
FIG. 7 is a partial block and partial schematic circuit diagram of an AC generator used in the embodiment of FIG. 6.

In FIG. 7, there is shown a partly block and partly schematic diagram of the pulse generator 160 having a crystal oscillator 180, a frequency divider 182, a sine wave generator 184 and a power amplifier 186. The crystal oscillator 180 and frequency divider 182 are electrically connected to provide square wave pulses of a relatively low frequency such as 244 or 275 hertz and have their output electrically connected to the sine wave generator 184. The sine wave generator 184 generate waves which are substantially sine waves for application to the power amplifier 186 to drive the differential pressure control and mixer 14 (FIGS. 1 and 6) and through conductor 196 to the synchronous detector 164 (FIG. 6).

To generate pulses, the crystal oscillator 180 is a conventional 2 megahertz crystal oscillator and the frequency divider 182 is a 8,192 to 1 frequency divider to produce 244 hertz. Both of these units are conventional and only intended to obtain a sufficiently low frequency for sensing by the differential pressure control and mixer 14 (FIGS. 2 and 6) which operates in a manner analogous to linear variable differential transformers. It has been found that using a low frequency of 275 hertz instead of 244 hertz may be advantageous because it causes less noise due to unwanted interaction with harmonics of 60 or 50 hertz power mains and 275 hertz may be produced by changing the crystal oscillator frequency to 2.253 megahertz.

The sine wave generator 184 includes a band pass filter 188, a 270 ohm resistor 190 and a 1 uf (microfarad) capacitor 192 connected in series with the filter 188 receiving the substantially 244 hertz square wave pulses from the frequency divider 182 to which it is connected and supplying a substantially sine wave output to the 270 ohm resistor 190 and the capacitor 192 in that order. The filter 188 is a filter having two low pass poles of sufficiently high Q to produce a sine wave and otherwise may be conventional. Conductor 196 receives the sine wave for application to the synchronous detector 164 (FIG. 6) and the linear power amplifier 186 receives the sine wave and applies it through a conductor 102 to the second coil 92 (FIG. 2) of the differential pressure control and mixer 14 (FIGS. 1 and 6) with conductor 128 serving as a ground connection in this circuit.

Figure 8:
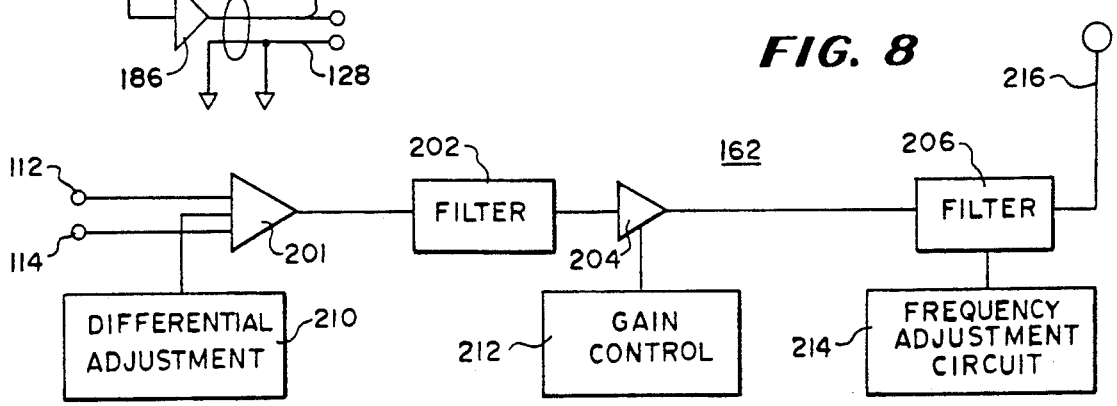
FIG. 8 is a block diagram of a circuit used for processing the output of the differential pressure measuring system of FIG. 2.

In FIG. 8, there is shown a partly block and partly schematic diagram of the equality signal former 162 which adjusts the sine wave output signal from the differential pressure control and mixer 14 (FIGS. 1 and 6) to have an amplitude and phase suitable for the synchronous detector 164 (FIG. 6). For this purpose, it includes an amplifier 201, a first filter 202, a second amplifier 204 and a second filter 206 connected in series in the order named between the output of the differential pressure control and mixer 14 (FIGS. 1 and 6) and the synchronous detector 164 (FIG. 6).

The amplifier 201 is a differential amplifier having one input electrically connected to conductor 112 and the other input electrically connected to conductor 114 from the first and third coils 90 and 94, respectively, of the differential pressure control mixer 14 (FIGS. 2 and 6). The output of the amplifier 201 provides a signal indicating the difference between the signal on conductor 112 and the signal on conductor 114 to the input of the filter 202.

The balance of the differential amplifier 201 is controlled by a conventional differential adjustment 210 for the purpose of zeroing its output in response to a particular potential between the conductors 112 and 114 which indicates a neutral position of the poppet 80 (FIG. 2). Preferably, the differential adjustment provides both phase and magnitude adjustment to provide a complete zero. Advantageously, this neutral position is taken with the poppet 80 just barely opening the outlet of the differential pressure control and mixer 14 but may be taken at other locations.

The filter 202 is a broad band filter centered at 244 hertz (or 275 hertz, in one embodiment) to preferably pass the frequency utilized in the differential pressure control and mixer 14 (FIGS. 1 and 6) for sensing. It supplies this signal to the second amplifier 204 which is a variable gain amplifier adjusted by a conventional gain control circuit 212.

For further selection and fine tuning of the frequency, the output of the second amplifier 204 is electrically connected to the input of the second filter 206 which is a narrow band filter. The second filter 206 may be set by adjusting its frequency adjustment circuit 214 such as by a screw driver on commercial units. The output of the second filter 206 is electrically connected to the synchronous detector 164 (FIG. 6) through a conductor 216. At the resonant frequency of a narrow band resonator, frequency adjustment causes more variation of phase than of amplitude. Therefore, this frequency adjustment is used to set the phase of the output signal on conductor 216. It is set so that its phase is the same as that of the synchronous detector 164 when the poppet 80 is just barely opening at pressure equality. This decreases noise.

Figures 9, 10:
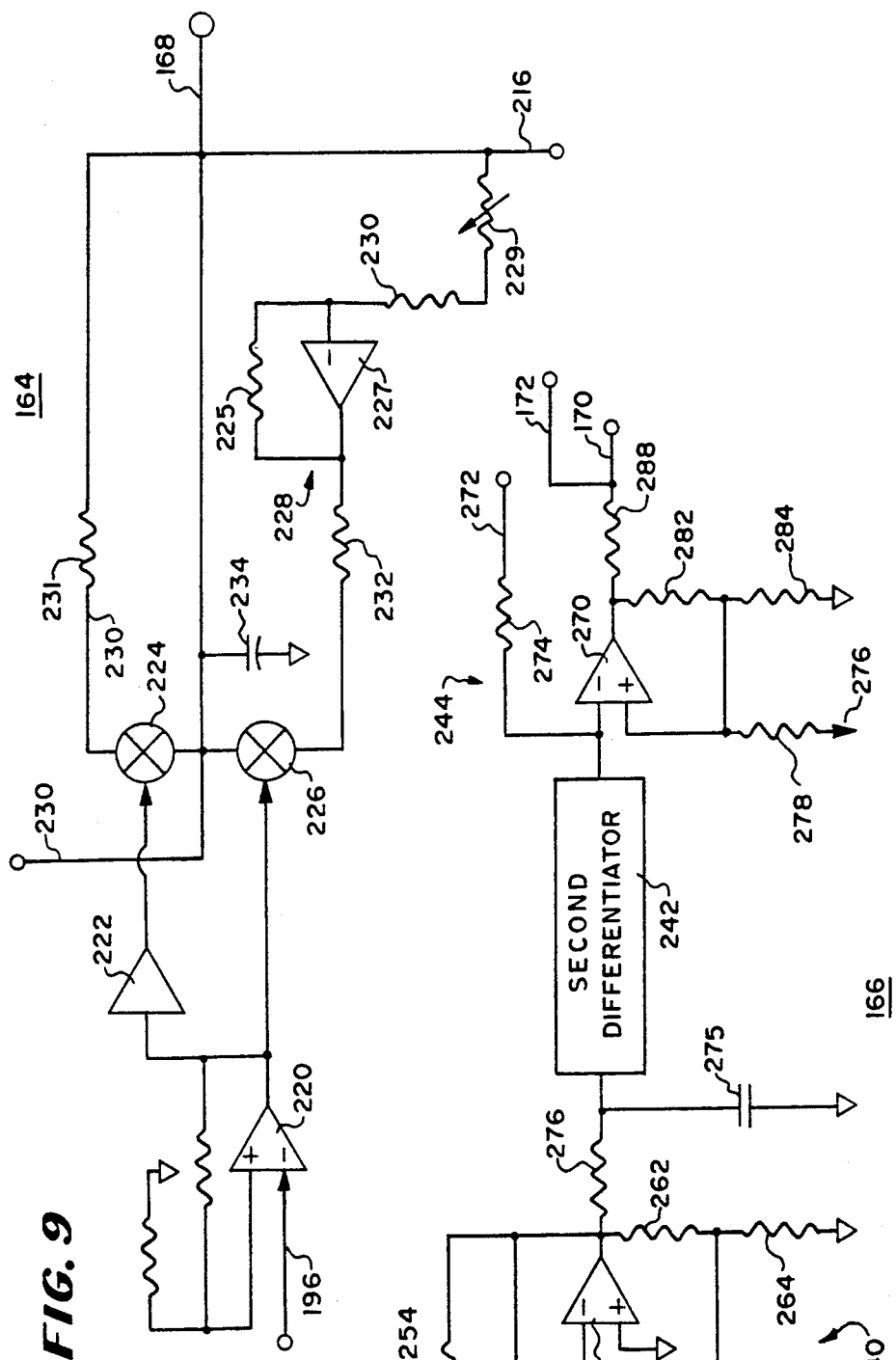
FIG. 9 is a schematic circuit diagram of a synchronous detector used in the embodiment of FIG. 5.
FIG. 10 is a schematic circuit diagram of a differentiator used in the embodiment of FIG. 5.

In FIG. 9, there is shown a schematic circuit diagram of the synchronous detector 164 having a Schmitt trigger 220, an inverter 222, first and second analog switches 224 and 226, and a unity gain amplifier 228 connected together to conduct pulses at substantially 244 hertz (or 275 hertz in one embodiment) only through the first and second analog switches 224 and 226 to the output conductor 230 and conductor 168 and thus remove unsynchronous noise. Conductor 230 is electrically connected to the differentiator 166 (FIG. 6).

To pass synchronously phased components of the sine waves on conductor 216 without regard to polarity to the output conductors 168 and 230, the input of the Schmitt trigger 220 is electrically connected through conductor 196 to the AC generator 160 (FIGS. 6 and 7) and its output electrically connected to the input of the inverter 222 and directly to the gate of the analog switch 226. The output of the inverter 222 is electrically connected to the gate of the first analog switch 224 so that the first and second analog switches 224 and 226 are opened in opposite phases (180 degrees different).

To transmit signals from the differential pressure control and mixer 14 (FIGS. 2 and 6) to the output conductors 230 and 168, the input conductor 216 from the equality signal former 162 (FIGS. 6 and 8) is electrically connected to the input terminal of the first analog switch 224 through a 10K (kilohm) resistor 231 and to the input terminal of the second analog switch 226 through a 10K resistor and through the inverting unity gain amplifier 228 which incorporates an operational amplifier 227 and resistors 225, 229 and 230. Adjustable 5K variable potentiometer 229 provides adjustability for exact unity gain in amplifier 228.

The outputs of the first and second analog switches 224 and 226 are electrically connected directly to conductor 230 for application to the differentiator 166 (FIG. 6) and to conductor 168 which is also connected to ground through the 5 uf capacitor 234 to remove the double frequency residual alternating current, which is approximately 488 hertz (or 550 hertz, in one embodiment).

In FIG. 10, there is shown a schematic circuit diagram of the differentiator 166 having a first differentiator 240, a second differentiator 242 and an output amplifier 244. The first differentiator 240, second differentiator 242 and output amplifier 244 are electrically connected in series in the order named from conductor 230 to output conductor 170.

With this arrangement, a signal in the form of a slope change on conductor 230 from the synchronous detector 164 (FIG. 6) indicates that the poppet 80 (FIG. 2) has moved to permit a second fluid to flow into the differential pressure control and mixer 14 (FIGS. 2 and 6). The output conductor 170 conducts a pulse formed from the second derivative of this signal to the central controller 154 (FIG. 5) to start the mixer control 156 (FIG. 5) and to start the gradient program followed by the single-stroke syringe pump system 16 and the single-stroke syringe pump system 18, which pump systems form the gradient by changing pumping speeds in coordination with the program.

To differentiate the signal received on conductor 230, the first differentiator 240 includes a differential operational amplifier 250 and two reverse back-to-back transdiodes 252. The differential amplifier 250 has its non-inverting input terminal grounded, its output terminal electrically connected to the second differentiator 242 and to its inverting input by a feedback path which includes resistor 254 and capacitor 256 in parallel. Conductor 230 is electrically connected to the in verting terminal through a 1 uf differentiating capacitor 258 which cooperates with an input resistor 260 connected between it and the inverting input terminal of the differential amplifier 250 and the feedback resistor 254 to differentiate the signal received on conductor 230. The capacitor 256 and resistor 254 produce a lowpass filter rolloff.

To prevent overload, a voltage limiter and a voltage divider are connected between the output of the differential amplifier 250 and its inverting input. The voltage divider is connected between the output of the differential amplifier 250 and ground and consists of a resistor 262 and a resistor 264 connected in series in that order between the output of the differential amplifier 250 and ground. One circumstance causing overload is overadjustment when changing the zero adjust 210 (FIG. 8).

To limit the output voltage of the differentiator 240 to substantially 5 volts, the collector of one of the transdiodes of the reverse back-to-back transdiode circuit 252 is electrically connected between the resistors 262 and 264 of the voltage divider, the collector of the other transistor being electrically connected between capacitor 358 and resistor 260. The resistor 260 limits the derivative gain and together provides an output compatible with the second differentiator 242 and the output circuit. The second differentiator 242 is identical to the first differentiator 240 and contains the same parts.

Since conductor 230 interconnects with the first and second analog switches 224 and 226 (FIG. 9), the resistors 230 and 232 (FIG. 9) and the capacitor 234 have the same low pass filtering time constant as that formed by the corresponding capacitor 275 and resistor 277 at the input to the second differentiator 242 to maintain the same low pass filter time constant at the inputs of each of the differentiators and regardless of which of the first and second analog switches 224 and 226 (FIG. 9) of the synchronous detector 164 (FIG. 9) are open.

The output amplifier 244 is a Schmitt trigger which includes a differential amplifier 270 having its inverting input terminal electrically connected to the output of the second differentiator 242 and to output conductor 272 through a 1K resistor 274. The non-inverting input terminal of the differential amplifier 270 is biased by a source of a negative 8 volts at 276 through a 6.8K resistor 278. The output of the differential amplifier 270 is electrically connected to conductor 170 through the 470 ohm resistor 288 and is also connected to ground through a voltage divider including the 47K resistor 282 and a 1.5K resistor 284 with the non-inverting input terminal of the amplifier 270 being electrically connected between them. The trigger action of output amplifier 244 discriminates against small noise pulses exiting second differentiator 242, yet provides an output pulse in response to the larger pulse from second differentiator 242 that indicates pressure equality.

With this arrangement, the first and second differentiators 240 and 242 are heavily band-limited by loss pass filters to improve their immunity to noise arising from undesired motion of the poppet 80 (FIG. 2) and from electrical and/or electronic noise. The output signal is a sharp pulse indicating the balance within 20 pounds per square inch difference in pressure from the different fluid sources to cause the gradient program to start.

Figure 11:
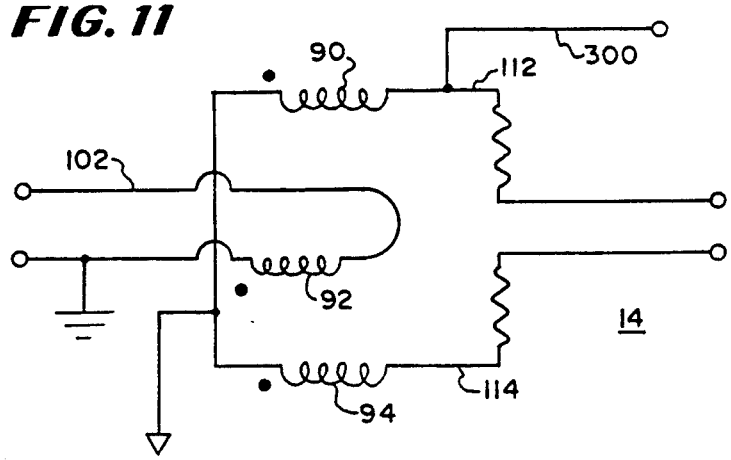
FIG. 11 is a schematic electrical diagram of a differential pressure measuring and mixing system such as that shown in FIG. 2.

In FIG. 11, there is shown a schematic circuit diagram of the differential pressure control and mixer 14 having the first, second and third coils 90, 92 and 94 with the second coil 92 being energized through conductor 102 and the first and third coils 90 and 94 being oppositely connected to induce opposing potentials therein which, if balanced, result in a net zero potential across conductors 112 and 114.

The first coil 90 is electrically connected to a conductor 300 which receives pulses, creating a magnetic field which lifts the poppet 80 (FIG. 2) upwardly away from the outlet end of the central chamber 42 (FIG. 2) and then permits it to fall back under pressure of gravity and the spring 82 (FIG. 2), thus causing stirring. The pulses are of sufficient current amplitude and the windings are sufficient in number to create a force on the poppet 80 (FIG. 2) that causes a substantial movement within the fluid. It is advantageous to use pulses of less than 30 percent duty factor.

Figure 12:
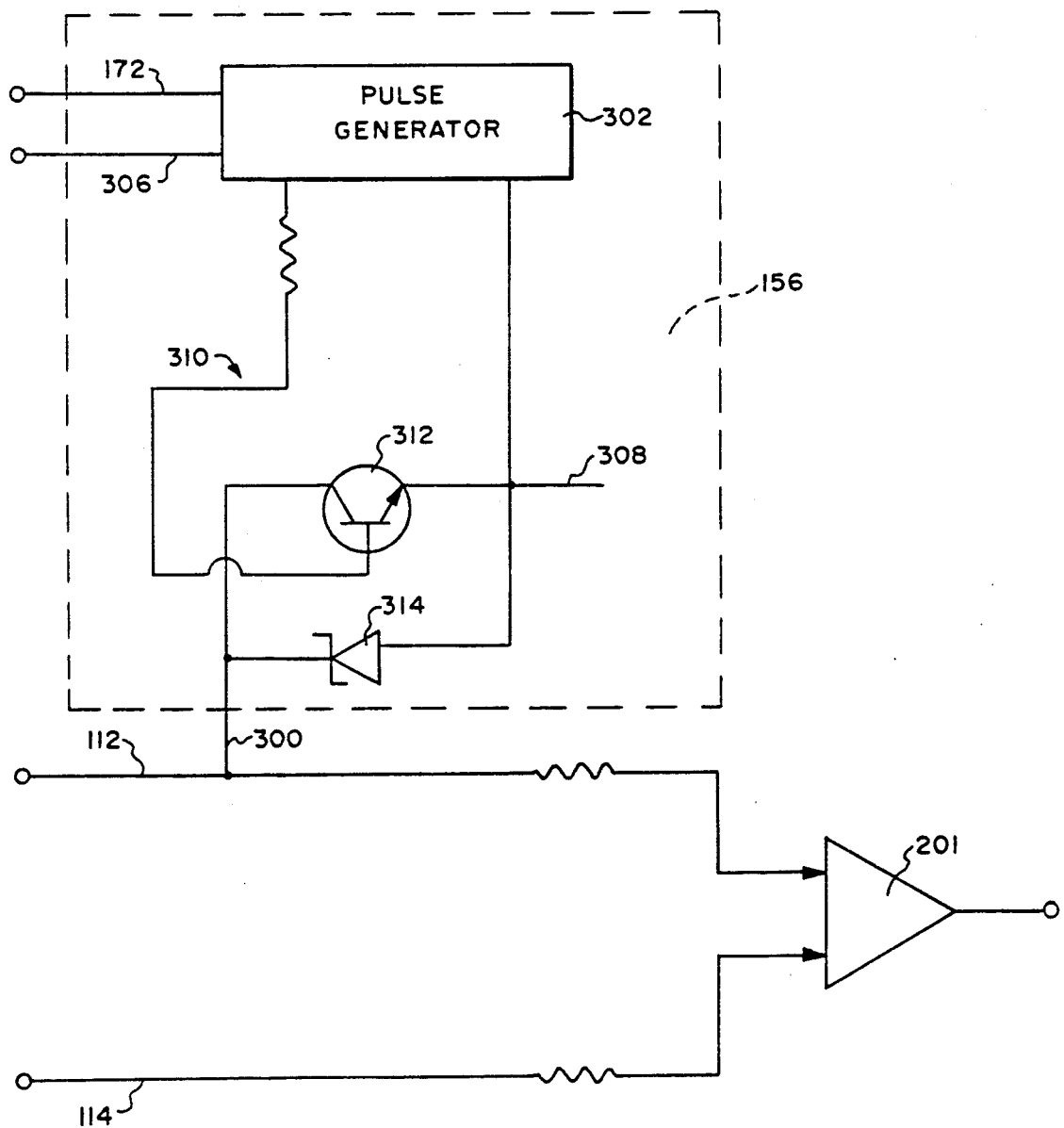
FIG. 12 is a schematic circuit diagram of a pulse circuit for driving the mixer of FIG. 2.

In FIG. 12, there is shown a schematic circuit diagram of the mixer control 156 having a pulse generator 302, a power supply 308, and a driver circuit 310. The pulse generator 302 is electrically connected to the equal pressure controller 150 (FIG. 5) through a conductor 172 and to the central controller 154 (FIG. 5) through a conductor 306 to initiate and terminate operation. The output of the mixer control 156 is electrically connected to the first coil 90 (FIGS. 2 and 11) through the conductor 300 and to one of the two inputs to the differential amplifier 201 (FIG. 8).

To provide pulses to conductor 300, the driver circuit 310 includes a 2N6292 NPN transistor 312 and a 1N4748A zener diode 314. The transistor 312 has: (1) its emitter electrically connected to the negative output terminal of a source of approximately a negative 12 volts 308, to the anode of the zener diode and to one output of the pulse generator 302; (2) its collector electrically connected to the cathode of the zener diode 314 and to conductor 300; and (3) its base electrically connected to the other output of the pulse generator 302 to receive positive going pulses therefrom. In response to pulses from the pulse generator 302, the driver 310 transmits current pulses of sufficient amplitude through the coil to move the poppet 80 (FIG. 2) a sufficient distance and at a sufficient rate for satisfactory mixing. In the preferred embodiment, the pulses are 12 volts, 100 millisecond pulses, occurring at a rate of twice per second.

It is believed that the mixer control function may be best provided by a computer controlling a driver. However, in an actual embodiment, the pulse generator 302 is a multivibrator sold by Global Specialties Corporation located in New Haven, Conn., under the designation model 4001 ultravariable pulse generator. Moreover, the pulse generator 302 may be any pulse generator having a relatively low frequency such as approximately 2 hertz, be susceptible of being turned on by a pulse on conductor 172 or by a pulse or voltage level change signal on conductor 306, and susceptible of being turned off by a pulse or voltage level change on conductor 306. There are many such pulse generators but any suitable astable multivibrator with an output gate controllable by pulses or voltage level changes on conductors 172 or 306 or any commercial integrated circuit having the equivalent of this functional unit may be used.

Before operating the chromatographic system 10, the system is zeroed at zero differential pressure, such as by venting both pumps to atmospheric pressure. Poppet 80 then rests lightly on O-ring 84 (FIG. 2). In this position, signals are generated by the AC generator 160 (FIGS. 6 and 7) to energize the second coil 92 through conductor 102 and the first and third coils by coupling with the second coil 92 (FIG. 2). The signals received from the first and third coils 90 and 94 on conductors 112 and 114 (FIGS. 2 and 11) are applied through the equality signal former 162 (FIGS. 6 and 8) while the differential adjustment 210 is adjusted until there is no output signal in the output 168 of the synchronous detector 164 (FIG. 6). The system is now zeroed.

In operation, the chromatographic system of this invention begins a chromatographic run with an initial composition fluid being pumped through the differential pressure control and mixer 14 (FIG. 1) to the chromatographic injector, column, detection and collection system 12 while the final composition fluid is prevented from flowing through the differential pressure control and mixer 14 until the pressures of the two are substantially equal. The gradient controller 152 (FIG. 5) then begins its programmed sequence for controlling the speed of the first and second single-stroke syringe pump systems 16 and 18 (FIG. 2) through a program intended to vary the composition of the fluids through tubes 52 and 54 (FIG. 2) in communication with the differential pressure control and mixer 14, which causes the fluids to be mixed before being sent through the outlet tube 76.

To pump the initial fluid through the outlet tubing 76 (FIG. 2) into the chromatographic injector, column, detection and collection system 12 (FIG. 1), the central controller 154 (FIG. 5) initiates action either under the control of an operator or, if it is a series of chromatographic runs, under the control of a program. It energizes the second single-stroke syringe pumping system 18 (FIG. 1) and the gradient controller 152 (FIG. 152) but the gradient controller 152 does not begin sequencing to control the speed of the pump motors in the first and second pumping systems 16 and 18 at this time.

The second single-stroke syringe pump system 18 has the initial fluid of the gradient to be pumped into the chromatographic injector, column, detection and collection system 12 (FIG. 1) and the first single-stroke syringe pump system 16 the last gradient so that the pump motor of the second single-stroke syringe pump system 18 begins pumping first and then slows down as the pump motor of the first single-stroke syringe pump system 16 increases so that in constant flow rate operation, the total flow rate through the outlet tubing 76 (FIG. 2) into the chromatographic injector, column, detection and collection system 12 is constant but the rate from each of the first and second single-stroke syringe pump systems 16 and 18 varies.

The first and second single-stroke syringe pumping systems 16 and 18 (FIG. 1) are syringe pumps which: (1) include in their cylinders a substantial amount of fluid; and (2) pump the fluid from their cylinders at a relatively smooth rate under varying pressure. During the beginning of the chromatographic run, the initial solvent flows through the column to initialize the column while there is no fluid flowing from the final gradient source. At this time, the fluid through tube 54 (FIG. 2) flows past the edge of the O-ring 84 along the sides of the poppet 80 through the clearance down to the space in the chamber 42 between the poppet 80 and the outlet fitting 34 and through the outlet tube 76 (FIG. 2). There is sufficient back pressure in the outlet tube 76 so that together with the spring 82 and the back pressure, the O-ring 84 is compressed and the poppet 80 forced back against the inlet fitting 32 with its central extending boss covering the outlet from the tubing 52 and the O-ring 84 being squeezed to provide a seal.

The flow of only the initial fluid continues while the first single-stroke syringe pump system 16 (FIG. 1) starts to pressurize its contents in the tube 52. The motor of the first single-stroke syringe pump system 16 generally runs faster than the rate corresponding to the initial composition of the mixed fluid at the programmed start of the chromatographic run.

Because of fluid compressibility in the first single-stroke syringe pump system 16, the motor builds up pressure in the cylinder gradually and when the pressure in the tubes 52 and 54 (FIG. 2) are close, such as within 100 pounds per square inch, the poppet 80 starts to move upwards, with the seal provided by O-ring 84 still being maintained by its resiliency. When the pressure difference between tubes 52 and 54 decreases further so that they are substantially equal, the seal between plug 32 and O-ring 84 opens and the differential pressure control and mixer 14 sends a signal through conductors 112 and 114 to the controller 20 (FIG. 1) to start a chromatographic run.

Amplifying upon this, when it is time to start the chromatographic run, the pressure in the tubes 52 and 54 (FIG. 2) are substantially equal, the resiliency of the O-ring 84 overcomes the force of gravity on the poppet 80 and the pressure of the spring 82 and the pressure of the fluid from the tube 52 and moves the poppet 80 upward toward the outlet fitting 34, permitting fluid to flow through the tube 52 through the chamber 42 around the poppet 80 to the outlet tube 76. At the time this flow first starts, the poppet 80 ceases or almost ceases to move forward toward the outlet fitting 34 and generates a signal before the fluid from the tube 52 reaches the outlet tube 76.

To generate a signal, the second coil 92 is energized with alternating current at a frequency of approximately 244 hertz from the AC generator 160 (FIGS. 6 and 7) which forms a sine wave and transmits it through conductor 102 to the central coil. The movement of the poppet 80 (FIG. 2) from its zero position causes a shift in the coupling between the second coil 92 and the first and third coils 90 and 94 which results in a potential between conductors 112 and 114, causing an output signal to be applied to conductor 216 at the output of the equality signal former 162 (FIGS. 6 and 8). This signal is applied to the synchronous detector where it is compared with the signal from the AC generator 160 (FIGS. 6 and 7), resulting in a low-noise signal being sent to the differentiator 166. The differentiator 166 transmits a signal to the central controller 154 (FIG. 5) through a conductor 170 to start the chromatographic run.

To generate signals when the pressures in tubes 52 and 54 (FIG. 2) are equal, the second coil 92 is energized while in its off-zero or high output signal condition and the pressure in tube 54 is much higher than that in tube 52. When the pressures have become equal and the poppet 80 moves toward the outlet fitting 34, the movement of the poppet 80 shifts the flux path and the coupling between the second coil 92 and the first and third coils 90 and 94 resulting in a lower level output signal to the equality signal former 162 (FIG. 6) on conductors 112 and 114. This results in change in the output signal on conductor 216 being applied to the synchronous detector 164 in the form of a sine wave having a frequency of 244 hertz.

The sine wave from the AC generator 160 (FIGS. 6 and 7) on conductor 196 at a frequency of 244 hertz and the sine wave from the equality signal former 162 at the same frequency are phase compared within the synchronous detector 164 to discriminate against noise at other frequencies and the resulting signal applied to the differentiator 166 through a conductor 230. The differentiator 166 transmits a signal through the conductors 170 and 172 to the mixer control 156 (FIG. 5) and the central controller 154 indicating the movement of the poppet 80 (FIG. 2).

The signal applied to the central controller 154 (FIG. 5) from the differentiator 166 (FIG. 6) causes it to send a signal to the gradient controller 152 to start the gradient program and to the first and second single-stroke syringe pump systems 16 and 18. The gradient controller now begins controlling the speed of the pumps in the first and second single-stroke syringe pump systems 16 and 18 to follow the programmed gradient. In the case of a constant flow rate gradient, the speed of the two pumps is varied with sum of the flow rates of the fluids from the first and second single-stroke syringe pump systems 16 and 18 remaining constant.

While an O-ring 84 has been described to permit motion of the poppet 80 to serve as a valve seat and valve element respectively, other valve seat means and valve element means can be used. Similarly, while the poppet 80 and coil section 86 (FIG. 2) of the sensing and control section 36 are described to detect the motion of the valve element many other detectors may be used. Generally, either or both of the valve element and valve seat should provide means for maintaining a seal as the pressures in the first and second conduits 52 and 54 (FIG. 2) approach equality but provide a signal such as by permitting some motion of the valve element. The sensing and control section should contain means for detecting the signal so that if motion of the valve element is the signal the means for detecting the signal should be sensitive enough to detect motion before the seal is broken but while the pressures are close to equality.

As the fluids flow through the tubes 52 and 54 (FIG. 2) with the fluid through the tube 54 flowing immediately around the edge of the poppet 80 and the fluid through the tube 52 flowing outwardly between the extending boss of the poppet 80 and the inlet fitting 32 and then through the space in the central chamber 42 between the poppet 80 and the side walls of the interior of the central chamber 42, they both are mixed and flow into the conduit 76 to the chromatographic injector, column, detection and collection system 12. At the t[me the fluids start flowing, a signal is also applied to the mixer control 156 (FIG. 5) to start mixing action.

To provide mixing, the pulse generator 302 is energized by a signal on conductor 172 (FIG. 12) to cause the mixer control 156 (FIG. 5) to apply pulses through conductor 300 to the first coil 90 (FIG. 2). The pulses create a sufficient magnetic force to move the poppet 80 against gravity and the force of spring 82 toward the outlet fitting 34 and at the end of the pulse the poppet 80 is released and falls by gravity and the force of spring 82 back toward the inlet fitting 32 to cause agitation in the central chamber 42 which mixes the fluid therein. The heat generated by the electrical pulses in the first coil 90 is released by convection aided by the open notches in the fins 122, 124 and 126 (FIGS. 3 and 4) of the spool 96 to maintain reasonable temperature equalibrium while the gradient flows through the differential pressure control and mixer 14.

When the chromatographic run is over under the control of the central controller 154 (FIG. 5), it signals the gradient controller 152 and the first and second single-stroke syringe pump systems 16 and 18 (FIG. 2) as well as the mixer control 156, thus causing the pulses to cease in the coil 90 and terminate mixing. In the case of supercritical fluid chromatography with pressure as well as solvent composition programming, pressure is released by the first pump system 16 so that the poppet 80 again receives fluid from the higher pressure tube 54 through the gap between it and the outlet fitting 34 to cause the poppet 80 to move against the O-ring 84 (FIG. 2) and block the inlet 52 in preparation for another chromatographic run. If the pressure is not to be changed, it will often not be necessary to do this pressure cycling before the next injection.

From the above description, it can be understood that the chromatographic system of this invention has several advantages, such as: (1) it can start a gradient with greater precision because fluid from both pumps are equalized before the start of the run; (2) backflow of solvent from one pump into the other is prevented; and (3) a better mixture is made of the fluids using a very small economical mixer suitable for microliquid chromatography and supercritical liquid chromatography.

Although a preferred embodiment of the invention has been described with some particularity, many modifications and variations are possible in the embodiment without deviating from the invention. Therefore, it is to be understood that, within the scope of the appended claims, the invention may be practiced other than as specifically described.

What is claimed is:

1. Apparatus comprising:
  means for receiving a first fluid;
  means for receiving a second fluid;
  means for sensing differences in pressure between said first and second fluids; and
  a fluid chamber;
  said means for sensing differences in pressure including a movable part loosely confined within the fluid chamber and means to sense motion of said movable part; and
  means to transmit a signal to a controller when the pressures of the fluid are equal, said controller having means to start a gradient run, upon receiving a signal, while permitting the proper composition of a gradient to flow and means to initiate stirring action within the apparatus for efficient mixing.

2. Apparatus in accordance with claim 1 further including means through which fluid from the fluid chamber flows after said first and second fluids have been mixed.

3. Apparatus according to claim 2 in which said means for sensing differences in pressure senses an electromagnetic field.

4. Apparatus in accordance with claim 3 in which said means for sensing differences in pressure and said loosely confined part includes a plurality of sensors spaced apart from each other.

5. Apparatus according to claim 4 in which:
  said movable part is a valve element means and said fluid chamber includes a valve seat means; and
  at least one of said valve element means and valve seat means includes means for permitting the valve element means to move with respect to the valve seat means without breaking a seal between the valve element means and the valve seat means, whereby said valve element means is moved against said valve seat means to block flow into said fluid chamber or away from said valve seat means to permit flow of the mixed fluids through said fluid chamber and whereby the said ability of the valve element to move with respect to the valve seat while maintaining a seal allows detection of the motion of the said valve element for sensing the said differences in pressure without unblocking the said fluids before the pressures are substantially equal.

6. Apparatus according to claim 5 in which the said means to sense motion produces an intermediate output indicative of the position of the valve element and said means to sense motion also incorporates a differentiator which produces the second derivative of the said intermediate output, wherein said second derivative is a signal pulse appearing when the said seal between the said valve element and the said valve seat breaks.

7. Apparatus according to claim 6 further including means for moving said valve element, whereby mixing of said fluids is aided.

8. Apparatus according to claim 1 in which said means for sensing differences in pressure senses an electromagnetic field.

9. Apparatus in accordance with claim 8 in which said means for sensing differences in pressure and said loosely confined part includes a plurality of sensors spaced apart from each other.

10. Apparatus according to claim 9 in which:
  said movable part is a valve element means and said fluid chamber includes a valve seat means; and
  at least one of said valve element means and valve seat means including means for permitting the valve element means to move with respect to the valve seat means without breaking a seal between the valve element means and the valve seat means, whereby said valve element means is moved against said valve seat means to block flow into said fluid chamber or away from said valve seat means to permit flow of the mixed fluids through said fluid chamber and whereby the said ability of the valve element to move with respect to the valve seat while maintaining a seal allows detection of the motion of the said valve element for sensing the said differences in pressure without unblocking the said fluids before the pressures are substantially equal.

11. Apparatus according to claim 10 in which the said means to sense motion produces an intermediate output indicative of the position of the valve element and said means to sense motion also incorporates a differentiator which produces the second derivative of the said intermediate output, wherein said second derivative is a signal pulse appearing when the said seal between the said valve element and the said valve seat breaks.

12. Apparatus according to claim 11 further including means for moving said valve element, whereby mixing of said fluids is aided.

13. Apparatus in accordance with claim 1 in which said means for sensing differences in pressure and said loosely confined part includes a plurality of sensors spaced apart from each other.

14. Apparatus according to claim 13 in which:
said movable part is a valve element means and said fluid chamber includes a valve seat means; and
at least one of said valve element means and valve seat means including means for permitting the valve element means to move with respect to the valve seat means without breaking a seal between the valve element means and the valve seat means, whereby said valve element means is moved against said valve seat means to block flow into said fluid chamber or away from said valve seat means to permit flow of the mixed fluids through said fluid chamber and whereby the said ability of the valve element to move with respect to the valve seat while maintaining a seal allows detection of the motion of the said valve element for sensing the said differences in pressure without unblocking the said fluids before the pressures are substantially equal.

15. Apparatus according to claim 14 in which the said means to sense motion produces an intermediate output indicative of the position of the valve element and said means to sense motion also incorporates a differentiator which produces the second derivative of the said intermediate output, wherein said second derivative is a signal pulse appearing when the said seal between the said valve element and the said valve seat breaks.

16. Apparatus according to claim 15 further including means for moving said valve element, whereby mixing of said fluids is aided.

17. Apparatus according to claim 1 in which:
said movable part is a valve element means and said fluid chamber includes a valve seat means; and
at least one of said valve element means and valve seat means including means for permitting the valve element means to move with respect to the valve seat means without breaking a seal between the valve element means and the valve seat means, whereby said valve element means is moved against said valve seat means to block flow into said fluid chamber or away from said valve seat means to permit flow of the mixed fluids through said fluid chamber and whereby the said ability of the valve element to move with respect to the valve seat while maintaining a seal allows detection of the motion of the said valve element for sensing the said differences in pressure without unblocking the said fluids before the pressures are substantially equal.

18. Apparatus according to claim 17 in which the said means to sense motion produces an intermediate output indicative of the position of the valve element and said means to sense motion also incorporates a differentiator which produces the second derivative of the said intermediate output, wherein said second derivative is a signal pulse appearing when the said seal between the said valve element and the said valve seat breaks.

19. Apparatus according to claim 18 further including means for moving said valve element, whereby mixing of said fluids is aided.

20. Apparatus according to claim 1 in which said movable part is a valve element; said apparatus further including means for moving said valve element, whereby mixing of said fluids is aided.

* * * * *